United States Patent [19]

Kraska et al.

[11] 4,180,700
[45] Dec. 25, 1979

[54] ALLOY COMPOSITION AND BRAZING THEREWITH, PARTICULARLY FOR CERAMIC-METAL SEALS IN ELECTRICAL FEEDTHROUGHS

[75] Inventors: Robert E. Kraska, Minneapolis; Joseph F. Lessar, Anoka, both of Minn.

[73] Assignee: Medtronic, Inc., Minneapolis, Minn.

[21] Appl. No.: 885,489

[22] Filed: Mar. 13, 1978

[51] Int. Cl.$^2$ .................. H01B 17/26; C03C 27/04; C22C 5/02
[52] U.S. Cl. .................. 174/152 GM; 65/59 B; 75/165; 228/122; 403/179
[58] Field of Search ............. 75/165, 134 V; 403/179, 403/28, 29, 30; 228/122, 903; 174/152 GM, 50.61; 428/432, 433, 434; 65/59 R, 59 B; 128/419 P

[56] References Cited

U.S. PATENT DOCUMENTS

| 1,107,180 | 8/1914 | von Oeffele | 75/165 |
| 1,107,181 | 8/1914 | von Oefele | 75/165 |
| 3,001,269 | 9/1961 | Moore et al. | 174/152 GM X |
| 3,063,144 | 11/1962 | Palmour | 174/152 GM X |
| 3,065,533 | 11/1962 | Dungan et al. | 174/152 GM X |
| 3,616,406 | 10/1971 | Turner | 75/165 X |

FOREIGN PATENT DOCUMENTS 937947 9/1963 United Kingdom ............. 75/165

*Primary Examiner*—Bruce A. Reynolds
*Assistant Examiner*—E. F. Borchelt
*Attorney, Agent, or Firm*—Schroeder, Siegfried, Ryan, Vidas, Steffey & Arrett

[57] ABSTRACT

New alloys containing gold, vanadium, yttrium and/or scandium, optionally including niobium. The alloys are particularly suitable for brazing and for metallizing, most particularly for brazing hermetic ceramic-metal seals. Unique brazing structures and methods are also disclosed.

15 Claims, 4 Drawing Figures

ALLOY COMPOSITION AND BRAZING THEREWITH, PARTICULARLY FOR CERAMIC-METAL SEALS IN ELECTRICAL FEEDTHROUGHS

BACKGROUND OF THE INVENTION

This invention relates to new alloys containing gold, vanadium, and, as a third constituent, yttrium or scandium or mixtures thereof. Additionally, the alloys may optionally contain niobium. In compositions including minor amounts of vanadium, yttrium and/or scandium, optional minor amounts of niobium, and a major amount of gold, the alloys are particularly useful as brazing materials and find a preferred use in the formation of hermetic corrosion-resistant seals or brazed joints for electrical lead-ins, particularly of the ceramic-metal seal types. The most preferred use of these alloys lies in the manufacture of ceramic-metal electrical lead-ins for implantable electromedical devices such as cardiac pacemakers and the like.

The invention also relates to the use of high gold content alloys for the metallization of ceramic materials such as alumina and other ceramics.

An important feature of the invention lies in the direct application of the brazing alloy to a ceramic-metal seal without prior metallization of the ceramic. For example, if the ceramic is alumina, it may be brazed with these alloys without prior metallization.

SUMMARY OF THE INVENTION

Broadly, this invention provides novel alloys of gold, vanadium, yttrium and/or scandium, optionally including niobium.

It has also been found, in accordance with this invention, that alloy compositions comprising a major portion of gold coupled with minor portions of vanadium and/or yttrium or scandium and optionally including niobium, provide excellent brazing and metallizing materials.

The alloys within the scope of this invention contain vanadium as an essential constituent. In the preferred compositions, the vanadium ranges from about 4 atomic percent up to about 15 atomic percent. Another essential constituent is selected from the group consisting of yttrium, scandium, and mixtures thereof. In the preferred alloy compositions, the yttrium and/or scandium ranges from about 0.008 atomic percent up to about 0.2 atomic percent. The optional constituent niobium is preferably present in minor amounts ranging from about 0 to about 3 atomic percent. The balance of the composition is gold, preferably in major amount. The percentages, as noted above, are expressed on an atomic percentage basis which is used throughout, unless otherwise noted.

In the most preferred alloy compositions of the invention, the amount of vanadium ranges from about 4% up to about 5% and the selected constituent yttrium and/or scandium ranges from about 0.008% up to about 0.02% in amount. If niobium is added, as optionally provided, it will preferably range between about 0% to about 3% in amount.

The most preferred alloy of the invention consists essentially of about 5% vanadium, about 0.02% yttrium, balance gold. Optionally, it may contain about 0.5% niobium.

The invention not only contemplates within its scope novel alloy compositions for various uses, but also novel brazed structures. The structural novelty of the brazed structures may arise either from the novel brazing alloy compositions used or from unique structural features described hereinbelow.

BRIEF DESCRIPTION OF DRAWINGS

FIG. 1 shows the structure before it is brazed. FIG. 2 shows the structure after it is brazed and mounted in an electrical device.

DESCRIPTION OF THE PREFERRED EMBODIMENTS

Figure 1:
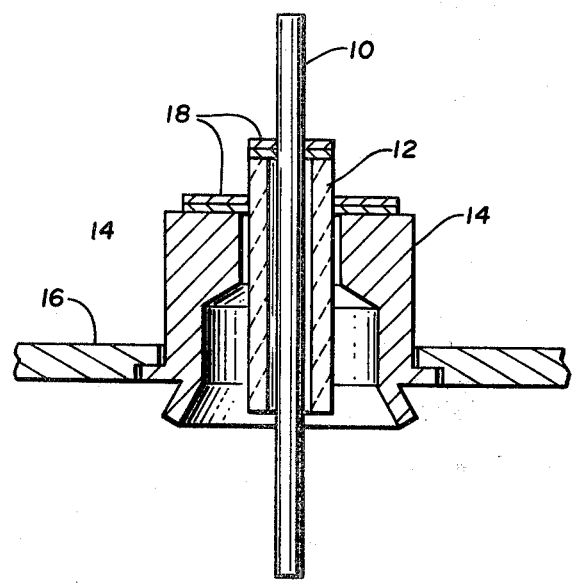
FIGS. 1 and 2 are cross sections of an electrical lead-in in the form of a ceramic-metal seal using an alloy of the invention.

As has already been pointed out, this invention relates in general to the use of high gold content alloys for the brazing and metallization of various ceramic materials, such as alumina ($Al_2O_3$), and various metals. Specifically, in its preferred form, it relates to the use of these alloys in the manufacture of ceramic-metal electrical lead-ins, particularly for implantable electro-medical devices such as cardiac pacemakers.

The alloys of the invention, as characterized by the nature of their constitutents, consist essentially of a carrier constituent, an active constituent, and a catalytic constituent. The carrier constituent comprises an element which imparts to the alloy the desired corrosion resistance and mechanical properties. In addition, in the case of implantable electromedical devices such as cardiac pacemakers, the carrier constituent must also provide biocompatability. The carrier constituent is the major component of the alloy. In the alloys of this invention, the carrier constituent is gold (Au).

The active constituent of the alloys of this invention consists of an element or elements which may chemically react with the material to be metallized or with one of the materials to be brazed. For example, in a preferred form of this invention, an alumina ceramic material is brazed to a metal and the active constituent of the alloy chemically reacts with the alumina and is thus responsible for the bonding of the ceramic to the metal.

The active constituent in accordance with the invention is selected from the class of metals commonly identified as strong oxide formers. Many metals exhibit a strong thermodynamic tendency to form oxides. However, the element selected for the alloys of this invention must also form a solid solution, i.e., a single phase structure with the carrier constituent. This requirement significantly limits the active elements which are suitable for a gold carrier constituent. The single phase microstructure ensures the retention of the desirable properties characterizing the carrier constituent of the alloy. Exceeding the solid solution solubility limit results in the formation of intermetallic compounds which generally impair the corrosion resistance and ductility of the alloys.

Of the various elements meeting the above requirements, it has been determined that only one element, i.e., vanadium (V), is satisfactory for the purposes of this invention. Vanadium has a solubility limit of approximately 15% in gold, which establishes the upper limit for this constituent in alloys according to this invention.

Other elements such as tantalum and hafnium, which exhibit very slight solubilities in gold as discussed above, are not acceptable except in incidental amounts since it has been determined that these elements do not significantly enhance wetting of the alloy when included in the alloys of the invention in any significant amount.

Various impurities may be present in the alloy in incidental amounts. It is preferred that they not exceed a total of about 0.1 wt. % of the total composition.

Another element, i.e., niobium (Nb), has been found to be an acceptable constituent when included in the alloys of the invention if its atomic percentage is maintained below about 3%.

However, the niobium is not a substitution for the vanadium, but comprises an optional addition to the overall composition. It does not affect wettability of the alloy in amounts below about 3% and it appears to improve corrosion resistance.

Another essential constituent of the alloys of this invention is the catalytic constituent which enhances the rate of the chemical reaction between the ceramic portion of a seal or lead-in structure and the active constituent of the alloy, i.e., the vanadium.

The most preferred catalytic constituent is yttrium (Y) which has been found to greatly accelerate the chemical reaction between a ceramic such as alumina and the vanadium and/or vanadium-niobium. The increased reaction rate may be due to the ability of yttrium to deoxidize vanadium, thus maintaining it in a highly chemically active state, or the yttrium may simply catalyze the reaction of the vanadium and the ceramic. An additional benefit realized from the yttrium addition is that it prevents the brazing alloy from "balling up" on the ceramic surface. Hence, the molten alloy will wet that portion of the ceramic with which it is in physical contact when in the solid state but will not flow on the surface thereof.

Scandium (Sc) has also been found to catalyze the reaction of the vanadium with ceramics. Scandium may be used to replace the yttrium or the two elements may be used mixed together in any proportion.

In assessing the upper and lower limits of the optimum compositional ranges for the various constituents in accordance with the invention, alloy wafers of about ⅜" in diameter were prepared. The wafers were placed upon sapphire sheets and heated to their melting point. The resultant samples were evaluated as to shape retention after being heated in excess of their melting point. Any substantial loss of shape was taken as being indicative of poor wetting and loss of bond area; both of which are unacceptable, particularly when a hermetic seal is desired.

Based on such tests, it was determined that when the amount of vanadium decreases below about 4%, a noticeable loss of "wetting" begins to develop. When the vanadium is increased above about 10-15%, no noticeable increase in "wetting" appears to occur, and the alloy suffers a noticeable loss of ductility and corrosion resistance. These properties appear to be optimal within the narrower range of from about 4% to about 5% vanadium.

With regard to the yttrium and/or scandium constituent, amounts below about 0.008% are difficult to measure reproducibly, and amounts greater than or equal to 0.2% tend to foster the formation of intermetallic compounds which decrease the corrosion resistance of the alloys and increase their brittleness. The optimum range was determined to be from about 0.008% to about 0.02%.

Amounts of niobium up to about 3% do not affect ductility or wettability. Furthermore, 0.5% Nb in Au—5V—0.02Y did not cause brittleness and is believed to improve the corrosion resistance of the alloy. The optimum amount was determined to be about 0.5% niobium.

It was established then that the alloys preferably contain: from about 4% up to about 15% vanadium; from about 0.008% up to about 0.2% of yttrium; the balance being gold.

However, scandium can be substituted in whole or in part for the yttrium, in the alloys.

The most preferred compositions will contain: about 5% vanadium; about 0.02% yttrium or equivalent (i.e., Sc substituted in whole or in part for Y); balance gold.

Additionally, in any of the compositions, niobium in an amount of from 0% to about 3%, 0.5% being preferred, can additionally be added to the other constituents.

Of the various alloys contemplated herein, the gold-vanadium-yttrium ternary alloy is the most preferred. The optimum composition for this ternary alloy is about 5% vanadium, about 0.02% yttrium, balance gold.

EXAMPLE 1

An alloy of Au—5% V—0.02% Y was placed on a sapphire substrate and melted. The contact angle for this alloy was less than 90°. It wet the sapphire rapidly and did not "ball-up" after melting.

EXAMPLE 2

An alloy of Au—5% V—0.02% Y was observed to have a microstructure which showed no evidence of intermetallic compound function when viewed at 1000×.

This alloy was flattened into a disc of approximately 0.015 inches thick and cut into a "half moon" shape. It was placed on a sapphire substrate and melted in vacuo. The alloy was observed to wet the substrate and retain its "half moon" shape.

EXAMPLE 3

Au—4.99% V—0.21% Y

Same treatment and results as for Example 2.

EXAMPLE 4

Au—5% V—0.008 Y

Same treatment and substantially the same results as for Example 2.

EXAMPLE 5

Au—4% V—0.02 Y

Same treatment and substantially the same results as for Example 2.

EXAMPLE 6

Au—5% V—0.02% Y

Same treatment and substantially the same results as for Example 2.

EXAMPLE 7

Au—5% V—0.02% Sc alloy formed into a disc of about 0.250 inches diameter and placed on a sapphire substrate.

Upon heating in vacuo to melting, the disc wet the sapphire and retained its original shape.

EXAMPLE 8

Au—5V—0.01% (Y+Sc) alloy—Same treatment and results as Example 8.

EXAMPLE 9

Au—5% V—0.5% Nb—0.02% Y Alloy—Same treatment and results as Example 8.

The alloys of the invention possess several advantages for use as a brazing material in forming ceramic-metal seals.

The alloys comprise a combination braze-metallization alloy for ceramics such as alumina. Metallization and brazing are accomplished in a single step during brazing.

The alloys exhibit excellent corrosion resistance and biocompatability. The alloys do not exhibit excessive flow properties.

The alloys exhibit a high degree of plasticity (fracture strain of about 20%) as well as low yield strength (about 12,000 psi) and ultimate tensile strength (about 30,000 psi) by virtue of the solid solution microstructure and the small degree of alloying needed to achieve bonding between the metal and ceramic in a seal or lead-in structure. These mechanical properties also tend to minimize thermal stresses which can induce cracking in the ceramic. Furthermore, these mechanical properties allow the alloy to be easily prepared by conventional methods.

The alloys flow readily but only by capillary action and readily metallize recesses in the joint between the ceramic and metal.

The interfacial bond between metal and ceramic is high quality, and there is no tendency for the braze to fracture the ceramic.

The alloy bonds to a wide variety of ceramics in addition to alumina (single crystal sapphire as well as polycrystalline alumina) such as carbon, forsterite, steatite, zircon, and mullite. Other refractory metal oxides such as zirconia, thoria, yttria, silica, and magnesia may also be considered for use.

In preparing the alloys of the invention, the gold and other constituents are charged onto a water-cooled copper hearth or chill plate, in weighed increments, in an arc melting furnace and melted in either an inert atmosphere such as argon or helium or in a vacuum to prevent contamination of the melt and loss of the constituents due to oxidation. The constituents may be melted several times for uniformity of the overall composition. The resulting melt is then solidified and prepared for use in any form desired by conventional working techniques. It may, for example, be rolled to foil thickness and cut to any desired shape.

In whatever form prepared, the alloy, when used as a brazing alloy, is positioned about the surfaces to be joined and placed in a furnace, the joint and surrounding brazing material are heated, in vacuo or under an inert atmosphere such as argon or helium, and held at temperature until the melted alloy is observed to melt and flow freely between the surfaces to be joined. At this point, the heating means is turned off and the melted alloy allowed to solidify to form the brazed joint.

The brazing alloys of this invention generally have a melting point of about 1960° F., and, when brazing, the temperature is usually raised to about 50° above the melting point of the alloy. Brazing at about 2000° to about 2025° F. for about two minutes from initial melting has been found to be satisfactory in brazing most ceramic-metal seals. The brazing operation must be conducted in a protective atmosphere, i.e., in vacuum (about $10^{-4}$ torr or less preferred) or under an inert atmosphere (dew point of about 90° F. or less preferred) such as helium or argon to reduce any contamination in the brazed joint or oxidation of the alloy constituents.

The parts to be brazed with the alloy should be cleaned and prepared by conventional physical or chemical methods before brazing. It is not necessary to metallize before brazing as excellent joints are prepared without this procedure.

As a brazing alloy, the alloys of this invention are capable of being used in a foil form or any preform shape. For example, a preform washer shape is preferred for electrical lead-ins of the coaxial type as are described hereinbelow.

Figure 2:
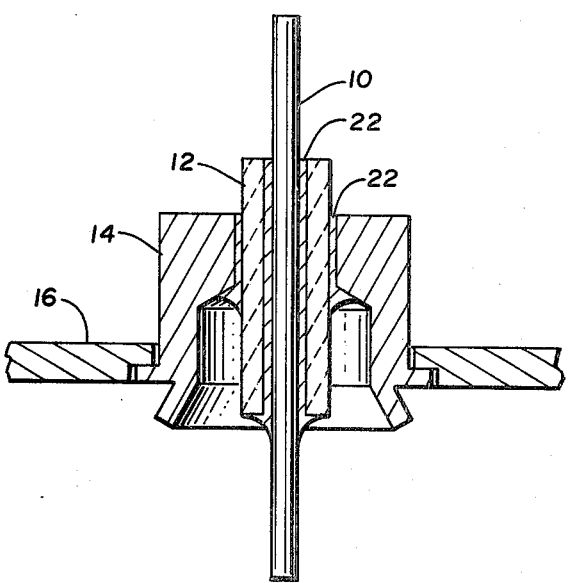

Referring now to FIGS. 1 and 2, an electrical lead-in incorporating a ceramic-metal seal prepared with the most preferred alloy of the invention is shown before and after brazing. The lead-in is oriented with the interior end thereof positioned upwardly in the figures. The lead-in comprises a central electrical conductor 10, which may take the form of a pin surrounded by a sapphire or alumina insulating body 12. Body 12 is encased in a metal ferrule 14 which, when the lead-in is installed in a device, may be welded or soldered into a wall 16 thereof as illustrated in FIG. 2. Pin 10 may be any conductive metal. However, in the case of an implantable medical device, it is preferred that the pin comprise niobium, tantalum, platinum, palladium, or titanium, niobium being preferred. Likewise, for such as application, alumina or sapphire is preferred for the ceramic, although, as pointed out herein above, other insulating ceramic-like materials may be used. The metal ferrule for implantable use is preferably titanium.

As can be seen in FIG. 1, to accomplish brazing, one or more preform washers 18 comprising an alloy of the invention, (V—5.5%, Y—0.2%, bal Au, for example) may be placed on ceramic body 12, surrounding pin 10, and on metal ferrule 14 surrounding ceramic body 12. The size of washer 18 and/or the number of washers used may vary as the flow of the liquid braze depends on the particular geometric characteristics of the article to be brazed.

Heating the assembly with the washer preforms positioned, as shown in FIG. 1, to a temperature of approximately 2000°-2025° F. for about two minutes in a protective atmosphere will, upon cooling, provide the brazed structure as shown in FIG. 2 having two brazed joints 22. The lead-in may then be welded or soldered into an opening in a device wall 16 as illustrated in FIG. 2.

Figure 3:
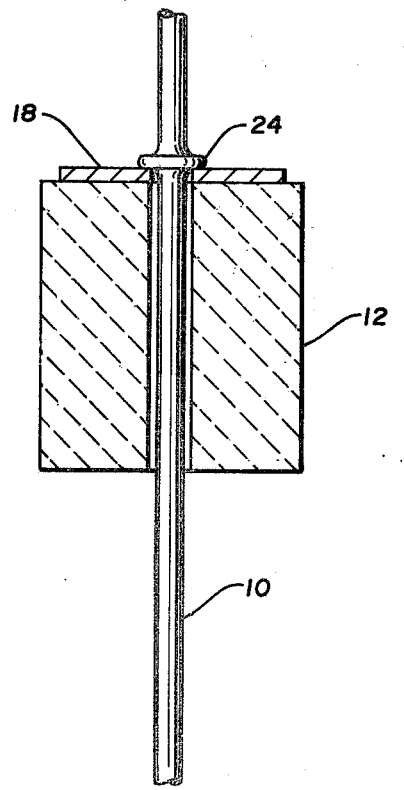
FIGS. 3 and 4 show, before and after brazing respectively, a unique structural feature for aiding the "wetting" of a brazing material in a ceramic-metal seal.
Figure 4:
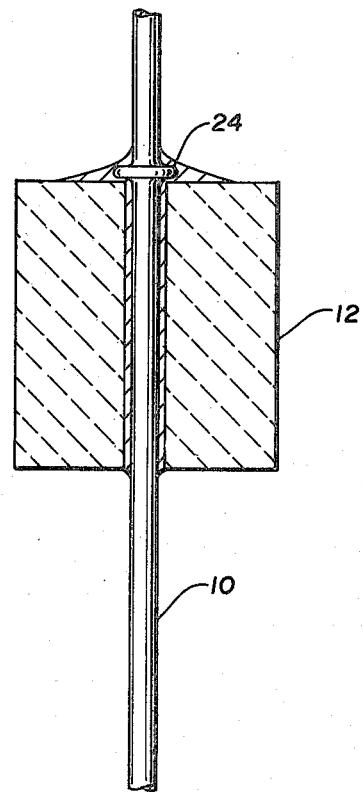

FIGS. 3 and 4 are illustrative of a preferred modification which may be used in electrical lead-in structures for facilitating the wetting of the brazing material to the conductive pin 10 and also for facilitating the flow of the melted brazed material into a joint area. Only the central pin 10 and the ceramic insulator 12 are shown in the figures. Pin 10 is provided with a peripherally extending shoulder means 24 which overlaps ceramic insulator 12 and contacts the brazing material preform 18. Preform 18 may be in the form of a washer as above described. Heating of the assembly to brazing temperature and cooling results in a brazed structure similar to that shown in FIG. 4 in which the flow of the brazing material into the joint area is facilitated by the contact between shoulder 24 and preform 18. Shoulder 24 may be simply formed by "upsetting" the pin using standard metal working techniques.

Corrosion resistance of the alloys of this invention was tested in two ways. Lead-ins brazed with representative alloy samples were subjected to life testing in pacemakers, and anodic polarization tests in accordance with ASTM G5—71 were conducted on other representative alloy samples.

Having described the invention by reference to preferred embodiments by way of illustration, exclusive property rights therein are defined by the following claims.

What is claimed is:

1. An article comprised of at least two members joined together by a thin alloy layer consisting essentially of vanadium, a constituent selected from the group consisting of yttrium, scandium, and mixtures thereof, the balance being gold and minor amounts of incidental impurities, if any.

2. The article of claim 1 wherein the alloy additionally includes niobium in an amount less than about 3% on an atomic percentage basis.

3. The article of claim 1 wherein the alloy consists essentially of minor amounts of vanadium and the selected constituent, the gold being predominant in amount.

4. The article of claim 1 wherein the alloy consists on an atomic percentage basis essentially of from about 4% up to about 15% vanadium, about 0.008% up to about 0.2% of a constituent selected from the group consisting of yttrium, scandium, and mixtures thereof, 0% up to about 3% niobium, the balance being essentially gold.

5. The article of claim 4 wherein the amount of vanadium ranges about 4% up to about 5% and the selected constituent ranges from about 0.008% up to about 0.02%.

6. The article of claim 5 wherein the amount of the selected constituent is about 0.02%.

7. The article of claim 6 wherein the selected constituent is yttrium.

8. An insulated coaxial lead-in for making electrical connection through a wall-like member, the lead-in comprising a central conductor and an outer sheath member, a generally cylindrical body of rigid insulating material separating the conductor and sheath and hermetically sealed to each by a first and second seal respectively, the seals comprising brazed joints formed of an alloy consisting essentially of vanadium, a constituent selected from the group consisting of yttrium, scandium, and mixtures thereof, the balance being essentially gold.

9. The article of claim 8 wherein the alloy additionally includes niobium in an amount less than about 3%, on an atomic percentage basis.

10. The article of claim 8 wherein the alloy consists essentially of minor amounts of vanadium and the selected constituent, the gold being predominant in amount.

11. The article of claim 8 wherein the central conductor includes a peripheral shoulder located in the area immediately above the brazed joint between said conductor and said body of rigid insulating material and overlapping the joint area.

12. The article of claim 8 wherein the alloy consists on an atomic percentage basis essentially of from about 4% up to about 15% vanadium, from about 0.008% up to about 0.2% of a constituent selected from the group consisting of yttrium, scandium, and mixtures thereof, from 0% up to about 3% niobium, the balance being essentially gold.

13. The article of claim 12 wherein the amount of vanadium ranges from about 4% up to about 5% and the selected constitutent ranges from about 0.008% up to about 0.02%.

14. The article of claim 13 wherein the amount of selected constituent is about 0.02%.

15. The article of claim 14 wherein the selected constituent is yttrium.

* * * * *